US011160867B2

(12) United States Patent
Duran

(10) Patent No.: US 11,160,867 B2
(45) Date of Patent: Nov. 2, 2021

(54) ANTI-PROTOZOAL COMPOUNDS AND USES THEREOF

(71) Applicant: AUBURN UNIVERSITY, Auburn, AL (US)

(72) Inventor: Sue H. Duran, Salem, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 152 days.

(21) Appl. No.: 15/977,211

(22) Filed: May 11, 2018

(65) Prior Publication Data

US 2018/0326072 A1 Nov. 15, 2018

Related U.S. Application Data

(60) Provisional application No. 62/504,721, filed on May 11, 2017.

(51) Int. Cl.
| | | |
|---|---|---|
| *A61K 47/34* | (2017.01) | |
| *A61K 31/53* | (2006.01) | |
| *A61K 31/4184* | (2006.01) | |
| *A61K 9/00* | (2006.01) | |
| *A61P 33/02* | (2006.01) | |

(52) U.S. Cl.
CPC ............ *A61K 47/34* (2013.01); *A61K 9/0034* (2013.01); *A61K 31/4184* (2013.01); *A61K 31/53* (2013.01); *A61P 33/02* (2018.01)

(58) Field of Classification Search
CPC ...... A61K 47/34; A61K 31/53; A61K 9/0034; A61K 31/4184; A61P 33/02
See application file for complete search history.

(56) References Cited

U.S. PATENT DOCUMENTS

| | | | | |
|---|---|---|---|---|
| 5,837,289 A | * | 11/1998 | Grasela ................ | A61K 9/0014 424/484 |
| 5,849,776 A | * | 12/1998 | Czernielewski ....... | A61K 31/70 514/398 |
| 2011/0245191 A1 | * | 10/2011 | Rosentel, Jr. .......... | A01N 43/90 514/30 |

FOREIGN PATENT DOCUMENTS

| | | | |
|---|---|---|---|
| EP | 0496316 | * | 7/1992 |
| FR | 2755824 | * | 5/1998 |

OTHER PUBLICATIONS

Drug Bank Metronidazole at https://www.drugbank.ca/drugs/DB00916 (retrieved from the internet Mar. 26, 2020) (Year: 2020).*
Chularojanamontri et al. in Journal of Clinical and Aesthetic Dermatology 7(5): 36-44 (2014) (Year: 2014).*
Almeida et al. in J Pharm Pharmaceut Sci. 15(4):592-605 (2012) (Year: 2012).*
Koziol J.H., In vitro efficacy of anti-protozoal compounds against Tritrichomonas foetus Master's Thesis at http://etd.auburn.edu/handle/10415/5227 (Jun. 17, 2016) (Year: 2016).*
Belgamwar et al. Asian Journal od Pharmaceutics (Jul.-Sep. 2008, p. 134-138 (Year: 2008).*
Lacey, E., The role of the cytoskeletal protein, tubulin, in the mode of action and mechanism of drug resistance to benzimidazoles. International journal for parasitology. 1988. 18, 885-936.
McCracken, R.O., Stillwell, W.H. A possible biochemical mode of action for benzimidazole anthelmintics. International journal for parasitology. 1991. 21, 99-104.
Dirikolu, L., Yohn, R., Garrett, E.F., Chakkath, T., Ferguson, D.C. Detection, quantifications and pharmacokinetics of toltrazuril sulfone (Ponazuril®) in cattle. Journal of Veterinary Pharmacology and Therapeutics. 2009. 32, 280-288.
Hosseinzadeh, H., Atyabi, F., Dinarvand, R., Ostad, S.N. Chitosan—Pluronic nanoparticles as oral delivery of anticancer gemcitabine: preparation and in vitro study. International Journal of Nanomedicine. 2012. 7, 1851-1863.
Kwon, G.S., Kataoka, K. Block copolymer micelles as long-circulating drug vehicles. Advanced Drug Delivery Reviews. 1995. 16, 295-309.
Kwon, G.S., Okano, T. Polymeric micelles as new drug carriers. Advanced Drug Delivery Reviews. 1996. 21, 107-116.
Leszczynska, K., Namiot, A., Cruz, K., Byfield, F.J., Won, E., Mendez, G., Sokolowski, W., Savage, P.B., Bucki, R., Janmey, P.A. Potential of ceragenin CSA-13 and its mixture with pluronic F-127 as treatment of topical bacterial infections. Journal of applied microbiology. 2011. 110, 229-238.
Bramwell, B.L., Williams, L.A. The use of Pluronic lecithin organogels in the transdermal delivery of drugs. International journal of pharmaceutical compounding. 2012. 16, 62-63.
Barichello, J.M., Morishita, M., Takayama, K., Nagai, T. Absorption of insulin from pluronic F-127 gels following subcutaneous administration in rats. International journal of pharmaceutics. 1999. 184, 189-198.
Dumortier, G., Grossiord, J.L., Agnely, F., Chaumeil, J.C. A review of poloxamer 407 pharmaceutical and pharmacological characteristics. Pharmaceutical research. 2006. 23, 2709-2728.
Pereira-Neves, A., Campero, C.M., Martinez, A., Benchimol, M. Identification of Tritrichomonas foetus pseudocysts in fresh preputial secretion samples from bulls. Vet Parasitol. 2011. 175, 1-8.
Pereira-Neves, A., Benchimol, M. Tritrichomonas foetus: Budding from Multinucleated Pseudocysts. Protist. 2009. 160, 536-551.
Pereira-Neves, A., Ribeiro, K.C., Benchimol, M. Pseudocysts in Trichomonads—New Insights. Protist. 2003. 154, 313-329.
De Andrade Rosa, I., De Souza, W., Benchimol, M. Changes in the structural organization of the cytoskeleton of Tritrichomonas foetus during trophozoite pseudocyst transformation. Micron. 2015. (Oxford, England : 1993) 73, 28-35.

* cited by examiner

*Primary Examiner* — Dennis Heyer
(74) *Attorney, Agent, or Firm* — Barnes & Thornburg LLP

(57) ABSTRACT

The present disclosure provides veterinary formulations comprising a therapeutically effective amount of an antiprotozoal compound and a polymer. The disclosure also provides methods of treating trichomoniasis in a bovine and methods of treating a *Tritrichomonas foetus* infection in a bovine utilizing the veterinary formulations.

20 Claims, 1 Drawing Sheet

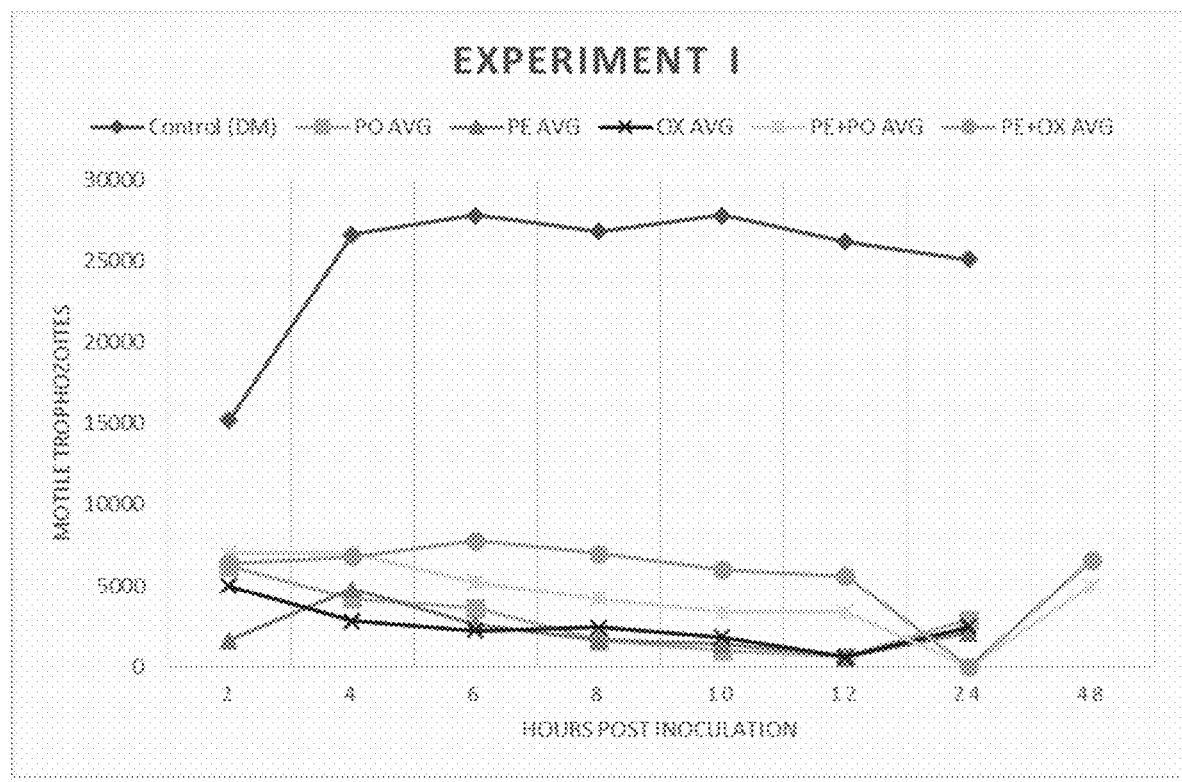

ANTI-PROTOZOAL COMPOUNDS AND USES THEREOF

CROSS-REFERENCE TO RELATED APPLICATIONS

This application claims the benefit under 35 USC § 119(e) of U.S. Provisional Application Ser. No. 62/504,721, filed on May 11, 2017, the entire disclosure of which is incorporated herein by reference.

TECHNICAL FIELD

The invention relates to veterinary formulations comprising a therapeutically effective amount of an antiprotozoal compound and a polymer. The invention includes compositions, methods, and formulations for the treatment of disease, such as for treating trichomoniasis in a bovine.

BACKGROUND AND SUMMARY OF THE INVENTION

Trichomoniasis is a sexually transmitted disease in cattle that is caused by the protozoa *Tritrichomonas foetus*. The organism is a single-celled, flagellated parasite that colonizes the epithelial crypts of the preputial mucosa in the preputial folds of bulls. Infected bulls are unaffected carriers of the organism, while cows can become infected during breeding. In cows, the disease is typically self-limiting, as the infection is commonly cleared in a few months after several heat cycles.

Trichomoniasis can cause significant impacts to a breeding herd. Infection in cows can result in endometritis, cervicitis, and vaginitis. The most common signs are related to infertility and can include early abortion with the cow returning to heat, repeated breeding resulting in a longer breeding season, various ranges of gestational ages at pregnancy check, and a significant reduction in calf crops with calving spread across a range of months.

In addition to reproductive impacts, trichomoniasis can cause significant economic losses for both beef and dairy cattle producers. The economic impact on the beef industry is estimated to be $2,000 to $2,500 per infected bull. Nationally, the disease has been estimated to reduce the calf crop by 2.5 percent (approximately 100,000 head). The economic impact of the calf crop reduction is estimated at approximately $100 million annually for cow-calf producers. If the losses are extended to the feedlot/finishing producers, the loss increases to over $150 million. Including the impacts of secondary and indirect losses, trichomoniasis is estimated to cost the industry approximately $300 million annually.

Currently, a vaccine for trichomoniasis is available for use in cows. However, the vaccine (TrichGuard) does not provide protection from infection with *T. foetus* and, instead, only reduces shedding of *T. foetus* organisms. Although vaccination programs can decrease the severity of clinical signs, they are unable to completely prevent abortion within a herd. In a recent vaccine trial, naïve heifers were vaccinated and subsequently challenged with *T. foetus*. Embryonic or fetal loss was detected in 9/19 (47%) vaccinated heifers and 10/14 (71%) sham vaccinated heifers (p=0.153) (Edmondson et al., *Theriogenology*, March 2017(90); 245-251). Furthermore, TrichGuard requires two doses administered two to four weeks apart, with a single, annual booster each subsequent year four weeks prior to the breeding season.

Moreover, an approved therapeutic option is not available for cows or bulls infected with *T. foetus*. Use of nitromidazoles, which have previously proven to be efficacious in clearing bulls infected with *T. foetus*, has been banned in the United States. With the lack of an effective FDA approved treatment, current recommendations are labor intensive and costly as infected bulls must be slaughtered.

Currently, *T. foetus* infection in bulls can only be prevented and controlled through the implementation of a biosecurity program, introduction of only virgin breeding stock for replacement animals, and periodic (annual) testing of bulls. If the infection is confirmed, all bulls should be tested with positive bulls culled from the herd. Three sequential negative tests taken one to two weeks apart are required to declare a bull clean. In addition, culling of all open cows after pregnancy diagnosis could also help minimize the risk of infection in the breeding herd. Although annual testing is recommended in bulls, there is a lack of sensitivity of the screening tests, which could still result in infection in the herd.

Therefore, there exists a need for new compositions and formulations that provide therapeutic options for treating trichomoniasis in cattle. Moreover, new and effective methods of treating *T. foetus* infection in cattle are also very desirable. Accordingly, the present disclosure provides veterinary formulations comprising a therapeutically effective amount of an antiprotozoal compound and methods of using the formulations, which exhibit desirable properties and provide related advantages for improvement in administration and treatment of cattle with trichomoniasis and *T. foetus* infection.

The present disclosure provides veterinary formulations comprising a therapeutically effective amount of an antiprotozoal compound and a polymer. The disclosure also provides methods of treating trichomoniasis in a bovine and methods of treating a *Tritrichomonas foetus* infection in a bovine utilizing the veterinary formulations.

The veterinary formulations and methods according to the present disclosure provide several advantages compared to other formulations and methods known in the art. First, the veterinary formulations comprise antiprotozoal compounds that are approved for use in food-producing animals, or have a known withdrawal time from extra-label use of a product from the USDA Food Animal Residue Avoidance Databank. Second, the veterinary formulations comprise a polymer for drug delivery that effectively disrupts the lipid layer of the stratum corneum, allowing therapeutic agents to pass through the stratum corneum and into the systemic circulation via the dermal-epidermal blood flow. Third, the veterinary formulations can result in complete eradication of infectious organisms with no reemergence of trophozoites or pseudocysts, and with cultures remaining negative, for several days following administration.

The following numbered embodiments are contemplated and are non-limiting:

1. A veterinary formulation comprising i) a therapeutically effective amount of an antiprotozoal compound and ii) a polymer.
2. The veterinary formulation of clause 1, wherein the antiprotozoal compound comprises a benzimidazole compound.
3. The veterinary formulation of clause 2, wherein the benzimidazole compound is oxfendazole.
4. The veterinary formulation of clause 2, wherein the benzimidazole compound is oxibendazole.
5. The veterinary formulation of clause 2, wherein the benzimidazole compound is albendazole.

6. The veterinary formulation of clause 1, wherein the antiprotozoal compound is ponazuril.

7. The veterinary formulation of clause 1, wherein the antiprotozoal compound is selected from the group consisting of oxfendazole, oxibendazole, albendazole, and ponazuril.

8. The veterinary formulation of clause 1, wherein the antiprotozoal compound is selected from the group consisting of oxfendazole, oxibendazole, and ponazuril.

9. The veterinary formulation of any one of clauses 1 to 8, with a proviso that the veterinary formulation does not comprise an isoxazoline compound.

10. The veterinary formulation of any one of clauses 1 to 9, wherein the veterinary formulation comprises one or more second therapeutic agents.

11. The veterinary formulation of clause 10, wherein the second therapeutic agent is selected from the group consisting of oxibendazole, oxfendazole, albendazole, and ponazuril, with the proviso that the second therapeutic agent of the formulation and the antiprotozoal compound of the formulation are not the same.

12. The veterinary formulation of clause 10, wherein the second therapeutic agent is an antibacterial compound.

13. The veterinary formulation of clause 10, wherein the second therapeutic agent is not an isoxazoline compound.

14. The veterinary formulation of any one of clauses 1 to 13, wherein the polymer comprises a polymer lecithin organogel.

15. The veterinary formulation of any one of clauses 1 to 14, wherein the polymer is a thermogel polymer.

16. The veterinary formulation of clause 15, wherein the thermogel polymer is selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly(N-vinyl n-butyramide) (PNVBAM), poly(N-vinyl caprolactam) (PNVCa), and poly (hydroxypropyl methacrylamide) (HPMA).

17. The veterinary formulation of clause 15, wherein the thermogel polymer is PolyVivo AK12.

18. The veterinary formulation of clause 15, wherein the thermogel polymer is PolyVivo AK24.

19. The veterinary formulation of clause 15, wherein the thermogel polymer is PolyVivo AK36.

20. The veterinary formulation of clause 15, wherein the thermogel polymer is PolyVivo AK088.

21. The veterinary formulation of clause 15, wherein the thermogel polymer is PolyVivo AK097.

22. The veterinary formulation of clause 15, wherein the thermogel polymer is PolyVivo AK100.

23. The veterinary formulation of clause 15, wherein the thermogel polymer is PolyVivo AK109.

24. The veterinary formulation of any one of clauses 15 to 23, wherein the polymer is a thermogel polymer at a temperature of about 30° C. to about 40° C.

25. The veterinary formulation of any one of clauses 15 to 23, wherein the polymer is a thermogel polymer at a temperature of about 33° C. to about 44° C.

26. The veterinary formulation of any one of clauses 15 to 23, wherein the polymer is a thermogel polymer at a temperature of about 31° C. to about 42° C.

27. The veterinary formulation of any one of clauses 15 to 23, wherein the polymer is a thermogel polymer at a temperature of about 27° C. to about 45° C.

28. The veterinary formulation of any one of clauses 1 to 27, wherein the veterinary formulation further comprises an emollient.

29. The veterinary formulation of clause 28, wherein the emollient comprises a cream.

30. The veterinary formulation of clause 28, wherein the emollient comprises an ointment.

31. The veterinary formulation of clause 28, wherein the emollient comprises a petrolatum.

32. The veterinary formulation of clause 28, wherein the emollient comprises a combination of petrolatum and mineral oil.

33. The veterinary formulation of clause 28, wherein the emollient comprises petrolatum and mineral oil in a water-miscible base.

34. The veterinary formulation of clause 28, wherein the emollient is Velcachol™.

35. The veterinary formulation of clause 28, wherein the emollient is combined with the antiprotozoal compound.

36. The veterinary formulation of clause 35, wherein the combination of the emollient and the antiprotozoal compound is performed prior to combination with the polymer.

37. The veterinary formulation of any one of clauses 1 to 36, wherein the veterinary formulation is a topical formulation.

38. The veterinary formulation of any one of clauses 1 to 37, wherein the veterinary formulation is single-use formulation.

39. The veterinary formulation of any one of clauses 1 to 37, wherein the veterinary formulation is a multi-use formulation.

40. The veterinary formulation of any one of clauses 1 to 39, wherein the veterinary formulation is an immediate release formulation.

41. The veterinary formulation of any one of clauses 1 to 39, wherein the veterinary formulation is an extended release formulation.

42. A method of treating trichomoniasis in a bovine, said method comprising the step of administering a veterinary formulation comprising i) a therapeutically effective amount of an antiprotozoal compound and ii) a polymer to the bovine.

43. The method of clause 42, wherein the veterinary formulation is the veterinary formulation of any one of clauses 1 to 41.

44. The method of clause 42 or 43, wherein the trichomoniasis is caused by *Tritrichomonas foetus*.

45. The method of clause 42 or 43, wherein the administration of the veterinary formulation reduces presence of a trichomoniasis-causitive agent in the bovine.

46. The method of clause 45, wherein the trichomoniasis-causitive agent is *Tritrichomonas foetus*.

47. The method of any one of clauses 42 to 46, wherein the bovine is a bull.

48. The method of any one of clauses 42 to 46, wherein the bovine is a heifer.

49. The method of any one of clauses 42 to 46, wherein the bovine is a cow.

50. The method of any one of clauses 42 to 49, wherein the trichomoniasis is caused by *Tritrichomonas foetus*.

51. The method of any one of clauses 42 to 50, wherein the administration is a topical administration.

52. The method of any one of clauses 42 to 50, wherein the administration is an intrauterine administration.

53. The method of any one of clauses 42 to 51, wherein the administration is applied to a location on the prepuce of the bovine.

54. The method of any one of clauses 42 to 51, wherein the administration is applied to a location on the penis of the bovine.

55. The method of any one of clauses 42 to 54, wherein the veterinary formulation is administered as a single unit dose.

56. The method of any one of clauses 42 to 54, wherein the veterinary formulation is administered as a multiple dose regimen.

57. The method of any one of clauses 42 to 56, wherein the method further comprises administration of one or more second therapeutic agents.

58. The method of any one of clauses 42 to 57, wherein the method of treating is performed until the *Tritrichomonas foetus* is no longer viable in the bovine.

59. The method of any one of clauses 42 to 58, wherein the method of treating is performed for a duration of one day.

60. The method of any one of clauses 42 to 58, wherein the method of treating is performed for a duration of two days.

61. The method of any one of clauses 42 to 58, wherein the method of treating is performed for a duration of three days.

62. The method of any one of clauses 42 to 58, wherein the method of treating is performed for a duration of four days.

63. The method of any one of clauses 42 to 58, wherein the method of treating is performed for a duration of five days.

64. The method of any one of clauses 42 to 58, wherein the method of treating is performed for a duration of six days.

65. The method of any one of clauses 42 to 58, wherein the method of treating is performed for a duration of seven days.

66. The method of any one of clauses 42 to 58, wherein the method of treating is performed for a duration of 10 days.

67. The method of any one of clauses 42 to 58, wherein the method of treating is performed for a duration of 14 days.

68. The method of any one of clauses 42 to 58, wherein the method of treating is performed for a duration of 21 days.

69. The method of any one of clauses 42 to 58, wherein the method of treating is performed for a duration of 28 days.

70. The method of any one of clauses 42 to 58, wherein the method of treating is performed for a duration of 30 days.

71. The method of any one of clauses 42 to 70, wherein the method of treating is performed one time per day.

72. The method of any one of clauses 42 to 58 or clauses 65 to 70, wherein the method of treating is performed one time per week.

73. The method of any one of clauses 42 to 58 or clauses 66 to 70, wherein the method of treating is performed one time per 10 days.

74. The method of any one of clauses 42 to 58 or clauses 67 to 70, wherein the method of treating is performed one time per every two weeks.

75. The method of any one of clauses 42 to 74, wherein the therapeutically effective amount of the antiprotozoal compound is at a dose of about 0.001 to about 1 mg/kg of weight of the bovine.

76. The method of any one of clauses 42 to 74, wherein the therapeutically effective amount of the antiprotozoal compound is at a dose of about 0.01 to about 0.1 mg/kg of weight of the bovine.

77. A method of treating a *Tritrichomonas foetus* infection in a bovine, said method comprising the step of administering a veterinary formulation comprising i) a therapeutically effective amount of an antiprotozoal compound and ii) a polymer to the bovine, wherein the administration of the veterinary formulation reduces one or more symptoms of the *Tritrichomonas foetus* infection in the bovine.

78. The method of clause 77, wherein the method of treating the *Tritrichomonas foetus* infection is a prophylactic treatment.

79. The method of clause 77 or clause 78, wherein the veterinary formulation is the veterinary formulation of any one of clauses 1 to 41.

80. The method of any one of clauses 77 to 79, wherein the bovine is a bull.

81. The method of any one of clauses 77 to 79, wherein the bovine is a heifer.

82. The method of any one of clauses 77 to 79, wherein the bovine is a cow.

83. The method of any one of clauses 77 to 82, wherein the administration is a topical administration.

84. The method of any one of clauses 77 to 82, wherein the administration is an intrauterine administration.

85. The method of any one of clauses 77 to 83, wherein the administration is applied to a location on the prepuce of the bovine.

86. The method of any one of clauses 77 to 83, wherein the administration is applied to a location on the penis of the bovine.

87. The method of any one of clauses 77 to 86, wherein the veterinary formulation is administered as a single unit dose.

88. The method of any one of clauses 77 to 86, wherein the veterinary formulation is administered as a multiple dose regimen.

89. The method of any one of clauses 77 to 88, wherein the method further comprises administration of one or more second therapeutic agents.

90. The method of any one of clauses 77 to 89, wherein the method of treating is performed until the *Tritrichomonas foetus* is no longer viable in the bovine.

91. The method of any one of clauses 77 to 90, wherein the method of treating is performed for a duration of one day.

92. The method of any one of clauses 77 to 90, wherein the method of treating is performed for a duration of two days.

93. The method of any one of clauses 77 to 90, wherein the method of treating is performed for a duration of three days.

94. The method of any one of clauses 77 to 90, wherein the method of treating is performed for a duration of four days.

95. The method of any one of clauses 77 to 90, wherein the method of treating is performed for a duration of five days.

96. The method of any one of clauses 77 to 90, wherein the method of treating is performed for a duration of six days.

97. The method of any one of clauses 77 to 90, wherein the method of treating is performed for a duration of seven days.

98. The method of any one of clauses 77 to 90, wherein the method of treating is performed for a duration of 10 days.

99. The method of any one of clauses 77 to 90, wherein the method of treating is performed for a duration of 14 days.

100. The method of any one of clauses 77 to 90, wherein the method of treating is performed for a duration of 21 days.

101. The method of any one of clauses 77 to 90, wherein the method of treating is performed for a duration of 28 days.

102. The method of any one of clauses 77 to 90, wherein the method of treating is performed for a duration of 30 days.

103. The method of any one of clauses 77 to 102, wherein the method of treating is performed one time per day.

104. The method of any one of clauses 77 to 90 or clauses 97 to 102, wherein the method of treating is performed one time per week.

105. The method of any one of clauses 77 to 90 or clauses 98 to 102, wherein the method of treating is performed one time per 10 days.

106. The method of any one of clauses 77 to 90 or clauses 99 to 102, wherein the method of treating is performed one time per every two weeks.

107. The method of any one of clauses 77 to 106, wherein the therapeutically effective amount of the antiprotozoal compound is at a dose of about 0.001 to about 1 mg/kg of weight of the bovine.

108. The method of any one of clauses 77 to 106, wherein the therapeutically effective amount of the antiprotozoal compound is at a dose of about 0.01 to about 0.1 mg/kg of weight of the bovine.

BRIEF DESCRIPTION OF THE DRAWINGS

FIG. 1 shows the inhibitory effects of various formulations on parasite growth over a 48 hour period post-inoculation. Averages for each assay were obtained by averaging the 5 replicates at the individual time points. Both ponazuril (PO) and oxibendazole (OX) alone demonstrated a 98% reduction in motile organisms after 2 hours of culture. However, following re-culture at 12 hours and examination at 24 hours, reestablishment of motile organisms was observed. A significant decrease in the number of trichomonads was also noted with pluronic lecithin organogel (PLO; Pluronic F127) polymer combined with OX and PLO combined with PO and their respective cultures were found to be negative for motile trophozoites at 24 hours post treatment. However, motile organisms were once again present at 48 hours with restoration of culture to original growth.

Various embodiments of the invention are described herein as follows. In one embodiment described herein, a veterinary formulation is provided. The veterinary formulation comprises i) a therapeutically effective amount of an antiprotozoal compound and ii) a polymer.

In another embodiment, a method of treating trichomoniasis in a bovine is provided. The method comprises the step of administering a veterinary formulation comprising i) a therapeutically effective amount of an antiprotozoal compound and ii) a polymer to the bovine.

In yet another embodiment, a method of treating a *Tritrichomonas foetus* infection in a bovine is provided. The method comprises the step of administering a veterinary formulation comprising i) a therapeutically effective amount of an antiprotozoal compound and ii) a polymer to the bovine, wherein the administration of the veterinary formulation reduces one or more symptoms of the *Tritrichomonas foetus* infection in the bovine.

In the various embodiments, the veterinary formulation comprises an antiprotozoal compound. Generally, antiprotozoal compounds refer to the class of pharmaceuticals used in treatment of protozoan infections. Furthermore, the veterinary formulation comprises a polymer. Polymers are well known in the art and generally refer to a substance that has a molecular structure consisting chiefly or entirely of a large number of similar units.

In the various embodiments, the antiprotozoal compound is present in the veterinary formulation at a therapeutically effective amount. As used herein, the term "therapeutically effective amount" refers to an amount which gives the desired benefit to an animal and includes both treatment and prophylactic administration. The amount will vary from one animal to another and will depend upon a number of factors, including the overall physical condition of the animal. The amount of the antiprotozoal compound used for the therapeutically effective amount gives an acceptable effect and maintains desired response at a beneficial level. A therapeutically effective amount of the composition used in the methods of the present disclosure may be readily ascertained by one of ordinary skill in the art using publicly available materials and procedures.

In various embodiments, the antiprotozoal compound comprises a benzimidazole compound. As known in the art, benzimidazoles are heterocyclic aromatic organic compounds that contain a fusion of benzene and imidazole. As used herein, the term "benzimidazole" refers to a benzimidazole base, pharmaceutically acceptable salts of a benzimidazole, other salts of a benzimidazole, metabolites of a benzimidazole, and prodrugs of a benzimidazole. The term "pharmaceutically acceptable salt" refers to an addition salt that exists in conjunction with the acidic or basic portion of a benzimidazole. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when a benzimidazole and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when a benzimidazole and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In some embodiments, the benzimidazole compound is oxfendazole. Oxfendazole is also known by chemical names such as methyl [5-(phenylsulfinyl)-1H-benzimidazol-2-yl] carbamate. The chemical structure of oxfendazole is:

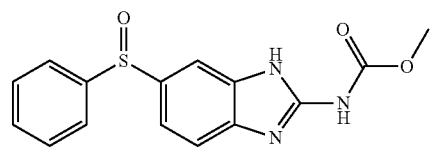 [SMILES: COC(=O)Nc1nc2ccc(S(=O)c3ccccc3)cc2[nH]1]

In other embodiments, the benzimidazole compound is oxibendazole. Oxibendazole is also known by chemical names such as methyl (5-propoxy-1H-benzimidazol-2-yl) carbamate. The chemical structure of oxibendazole is:

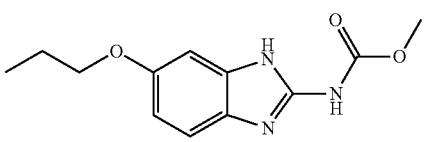 [SMILES: CCCOc1ccc2nc(NC(=O)OC)[nH]c2c1]

In yet other embodiments, the benzimidazole compound is albendazole. Albendazole is also known by chemical names such as methyl hydrogen [6-(propylsulfanyl)-1H-benzimidazol-2-yl]carboximidate. The chemical structure of albendazole is:

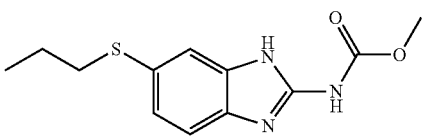 [SMILES: CCCSc1ccc2nc(NC(=O)OC)[nH]c2c1]

In some embodiments, the antiprotozoal compound is ponazuril. Ponazuril is also known by chemical names such as 1-Methyl-3-(3-methyl-4-(4-((trifluoromethyl)sulfonyl)phenoxy)phenyl)-1,3,5-triazinane-2,4,6-trione. The chemical structure of ponazuril is:

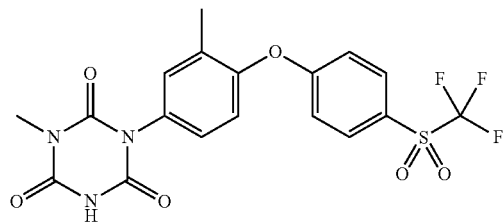 [SMILES: Cc1cc(-n2c(=O)[nH]c(=O)n(C)c2=O)ccc1Oc1ccc(S(=O)(=O)C(F)(F)F)cc1]

In certain aspects, the described veterinary formulation has a proviso that the veterinary formulation does not comprise an isoxazoline compound. In some embodiments, the antiprotozoal compound is selected from the group consisting of oxfendazole, oxibendazole, albendazole, and ponazuril. In other embodiments, the antiprotozoal compound is selected from the group consisting of oxfendazole, oxibendazole, and ponazuril.

In various embodiments, the veterinary formulation comprises one or more second therapeutic agents. In some embodiments, the second therapeutic agent is selected from the group consisting of oxibendazole, oxfendazole, albendazole, and ponazuril, with the proviso that the second therapeutic agent of the formulation and the antiprotozoal compound of the formulation are not the same.

In some embodiments, the second therapeutic agent is an antibacterial compound. In some embodiments, the second therapeutic agent is not an isoxazoline compound.

In various embodiments, the polymer comprises a polymer lecithin organogel. A polymer lecithin organogel ("PLO") is an opaque, yellow preparation comprising isopropyl palmitate or isopropyl myristate, soya lecithin, water, and Pluronic® F-127 ("PF127"; BASF, Ludwigshafen, Germany). PF127 is also known as poloxamer 407 (P407), (copolymer polyoxyethylene106-polyoxypropylene70-polyoxyethylene106) and contains about 70% ethylene oxide, which contributes to its hydrophilicity. PF-127 is a copolymer with a weight of 12,000 daltons, a PEO/PPO ratio of 2:1, and is non-toxic, with low viscosity below 4° C. and forms a semi-solid gel at body temperature. Other sources of PLO formulations are also contemplated and may be utilized for the described embodiments.

PLO includes an oil phase (lecithin dissolved in isopropyl palmitate in a 1:1 ratio) and an aqueous phase (aqueous solution of 20-30% of PF-127). The oil phase can be prepared by combining lecithin and isopropyl palmitate or isopropyl myristate and allowing the combination to stand overnight to ensure complete dissolution. The aqueous phase can be prepared by combining PF-127 and cold water, placing the combination in a refrigerator, and agitating periodically to ensure dissolution. Sorbic acid at 0.2% (w/w) or potassium sorbate may be added to the two phases as preservatives. The oil phase can be combined with the aqueous phase using a high-shear mixing method.

In various embodiments, the polymer is a thermogel polymer. Thermogel polymers (aka "thermogels") are generally known in the art as polymers that exist in liquid phase when refrigerated and exist in solid phase when at room temperature. Typically, the steric hindrance of thermogel polymers combined with a low molecular weight prevents crystallization, and therefore provides their thermosensitivity.

In some embodiments, the thermogel polymer is selected from the group consisting of poly(ethylene glycol) (PEG), poly(propylene glycol) (PPG), poly (N-isopropyl acrylamide) (PNIPAAm), poly(N,N-diethyl acrylamide) (PDEAM), poly(N-ethyl methacrylamide) (PNEMAM), poly(methyl vinyl ether) (PMVE), poly(2-ethoxyethyl vinyl ether) (PEOVE), poly(N-vinyl isobutyramide) (PNVIBAM), poly (N-vinyl n-butyramide) (PNVBAM), poly(N-vinyl caprolactam) (PNVCa), and poly (hydroxypropyl methacrylamide) (HPMA).

In certain embodiments, the thermogel polymer is PolyVivo AK12 (PLGA-PEG-PLGA, 1500-1000-1500 1:1 LA:GA):

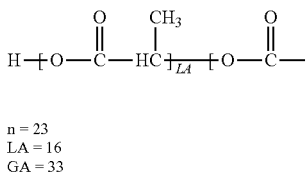

n = 23
LA = 16
GA = 33

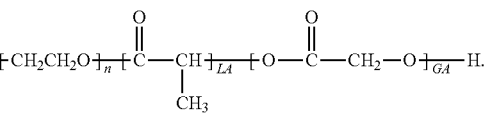

In other embodiments, the thermogel polymer is PolyVivo AK24 (PLGA-PEG-PLGA, 1500-1000-1500 3:1 LA:GA). In yet other embodiments, the thermogel polymer is PolyVivo AK36:

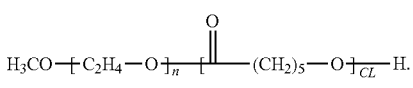

n = 18
CL = 22

In some embodiments, the thermogel polymer is Poly-Vivo AK088. PolyVivo AK088 is a thermogel polymer that is characterized as being a gel from 30-40° C. (max ~35° C.) and has a relatively quick degradation (~1-2 weeks) due to higher glycolide content. In other embodiments, the thermogel polymer is PolyVivo AK097. PolyVivo AK097 is a thermogel polymer that is characterized as being a gel from 33-44° C. (max ~39° C.) and has a moderate degradation (~2 weeks) due to high lactide content. In yet other embodiments, the thermogel polymer is PolyVivo AK100. PolyVivo AK100 is a thermogel polymer that is characterized as being a gel from 31-42° C. (max ~37° C.) and has a slower degradation (~2-3 weeks) as it is totally lactide. In other embodiments, the thermogel polymer is PolyVivo AK109. PolyVivo AK109 is a thermogel polymer that is characterized as being a gel from 27 to >45° C. (max ~36° C.) and has a very slow degradation (~1 month) as the PLCL chains are slow to degrade.

In various aspects, the polymer is a thermogel polymer at a temperature of about 30° C. to about 40° C. In other aspects, the polymer is a thermogel polymer at a temperature of about 33° C. to about 44° C. In yet other aspects, the polymer is a thermogel polymer at a temperature of about 31° C. to about 42° C. In other aspects, the polymer is a thermogel polymer at a temperature of about 27° C. to about 45° C.

In various embodiments, the veterinary formulation further comprises an emollient. Generally, an emollient is known in the art as an agent used on skin or mucous membranes for softening. Emollients can come in the form of creams, ointments, lotions, gels, and the like.

In some embodiments, the emollient comprises a cream. In other embodiments, the emollient comprises an ointment. In yet other embodiments, the emollient comprises a petrolatum. In some embodiments, the emollient comprises a combination of petrolatum and mineral oil. In other embodiments, the emollient comprises petrolatum and mineral oil in a water-miscible base. In yet other embodiments, the emollient is Velcachol™.

In some aspects, the emollient is combined with the antiprotozoal compound. In other aspects, the combination of the emollient and the antiprotozoal compound is performed prior to combination with the polymer.

In various embodiments, the veterinary formulation is a topical formulation. In some embodiments, the veterinary formulation is single-use formulation that is intended to be given to an animal in a single administration. In other embodiments, the veterinary formulation is multi-use formulation that is capable of being given to an animal in a single administration or in multiple administrations. Two or more polymers may be combined to achieve the correct temperature for the most efficacious product or for the desired immediate and/or extended release times as described below.

In some embodiments, the veterinary formulation is an immediate release formulation. An immediate release formulation is intended to quickly release the antiprotozoal compound of the veterinary formulation to the animal. In other embodiments, the veterinary formulation is an extended release formulation. An extended release formulation is intended to more slowly release the antiprotozoal compound of the veterinary formulation to the animal.

In another embodiment, a method of treating trichomoniasis in a bovine is provided. The method comprises the step of administering a veterinary formulation comprising i) a therapeutically effective amount of an antiprotozoal compound and ii) a polymer to the bovine. The previously described embodiments of the veterinary formulation are applicable to the method of treating trichomoniasis in a bovine described herein.

Trichomoniasis in bovine is a venereal disease by a protozoa organism. In certain aspects, the trichomoniasis is caused by *Tritrichomonas foetus*. As generally known in the art, *Tritrichomonas foetus* is a species of single-celled flagellated parasites that is known to be a bovine pathogen. In some aspects, the administration of the veterinary formulation reduces presence of a trichomoniasis-causitive agent in the bovine.

Bovines include animals from the biological subfamily Bovinae, which includes a diverse group of medium to large-sized ungulates, including domestic cattle, bison, African buffalo, the water buffalo, the yak, and the four-horned and spiral-horned antelopes. In some embodiments, the bovine are cattle. Cattle may be bulls, heifers, or cows. In one embodiment, the bovine is a bull. In another embodiment, the bovine is a heifer. In yet another embodiment, the bovine is a cow.

In some embodiments, the administration is a topical administration. In other embodiments, the administration is an intrauterine administration. In various embodiments, the administration is applied to a location on the prepuce of the bovine. In yet other embodiments, the administration is applied to a location on the penis of the bovine.

In some aspects, the veterinary formulation is administered as a single unit dose. In other aspects, the veterinary formulation is administered as a multiple dose regimen.

In various embodiments, the method further comprises administration of one or more second therapeutic agents. In one aspect, the method of treating is performed until the *Tritrichomonas foetus* is no longer viable in the bovine.

In some embodiments, the method of treating is performed for a duration of one day. In another embodiment, the method of treating is performed for a duration of two days. In yet another embodiment, the method of treating is performed for a duration of three days. In some embodiments, the method of treating is performed for a duration of four days. In another embodiment, the method of treating is performed for a duration of five days. In yet another embodiment, the method of treating is performed for a duration of six days. In some embodiments, the method of treating is performed for a duration of seven days. In another embodiment, the method of treating is performed for a duration of 10 days. In yet another embodiment, the method of treating is performed for a duration of 14 days. In some embodiments, the method of treating is performed for a duration of 21 days. In another embodiment, the method of treating is performed for a duration of 28 days. In yet another embodiment, the method of treating is performed for a duration of 30 days.

In some embodiments, the method of treating is performed one time per day. In another embodiment, the method of treating is performed one time per week. In yet another embodiment, the method of treating is performed one time per 10 days. In some embodiments, the method of treating is performed one time per every two weeks.

In some embodiments of the method, the therapeutically effective amount of the antiprotozoal compound in the veterinary formulation is administered to the animal at a dose of about 0.001 to about 1000 mg of antiprotozoal compound per kg of animal body weight. In one embodiment, the therapeutically effective amount of antiprotozoal compound in the veterinary formulation is administered to the animal at a dose of about 0.001 to about 100 mg of antiprotozoal compound per kg of animal body weight. In another embodiment, the therapeutically effective amount of antiprotozoal compound in the veterinary formulation is administered to the animal at a dose of about 0.01 to about 100 mg of antiprotozoal compound per kg of animal body weight. In yet another embodiment, the therapeutically effective amount of antiprotozoal compound in the veterinary formulation is administered to the animal at a dose of about 0.1 to about 100 mg of antiprotozoal compound per kg of animal body weight. In one embodiment, the therapeutically effective amount of antiprotozoal compound in the veterinary formulation is administered to the animal at a dose of about 0.1 to about 10 mg of antiprotozoal compound per kg of animal body weight. In another embodiment, the therapeutically effective amount of antiprotozoal compound in the veterinary formulation is administered to the animal at a dose of about 1 to about 5 mg of antiprotozoal compound per kg of animal body weight.

In yet another embodiment, a method of treating a *Tritrichomonas foetus* infection in a bovine is provided. The method comprises the step of administering a veterinary formulation comprising i) a therapeutically effective amount of an antiprotozoal compound and ii) a polymer to the bovine, wherein the administration of the veterinary formulation reduces one or more symptoms of the *Tritrichomonas foetus* infection in the bovine. The previously described embodiments of the veterinary formulation and of the method of treating trichomoniasis in a bovine are applicable to the method of treating a *Tritrichomonas foetus* infection in a bovine described herein.

In certain aspects, the method of treating the *Tritrichomonas foetus* infection is a prophylactic treatment. As used herein, the term "prophylactic treatment" refers to either preventing or inhibiting the development of a clinical condition or disorder or delaying the onset of a pre-clinically evident stage of a clinical condition or disorder. The term is to be understood as meaning that the veterinary formulations according to the present disclosure can be applied before symptoms of the *Tritrichomonas foetus* infection are manifest.

EXAMPLES

Anti-Protozoal Compositions

Various veterinary formulations comprising a therapeutically effective amount of an antiprotozoal compound and a polymer were prepared for testing. Three different antiprotozoal compounds were individually combined with the exemplary polymer pluronic lecithin organogel ("PLO"; Pluronic F127, Letco Medical, Decatur, Ala.) to form three different veterinary formulations.

Parasites and Cultures

Experiments were performed in vitro using pure cultures of *T. foetus* trophozoites with the addition of i) an antiprotozoal compound alone or ii) a veterinary formulation comprising an antiprotozoal compound and a polymer. Samples were evaluated at predetermined time points using Neubauer hemocytometers (C-Chip® NanoEnTek Inc., Pleasanton, Calif.) to determine the number of viable organisms and the induction of the pseudocyst form. Cultures were tested for reversibility to the motile trophozoite form or replication of organisms.

The CDTf3 cloned strain of *T. foetus* was utilized for the instant examples. The parasites were cultivated in trypticase-yeast extract-maltose (TYM) Diamond's medium (DM) and supplemented with 10% heat-inactivated fetal bovine serum (Atlanta Biologics, Norcross, Ga.) at 37° C. for 24-48 hours until adequate numbers of trichomonads were present to perform the required number of replications. Following culture, *T. foetus* organisms were washed and re-suspended in 1 mL of sterile phosphate buffered saline (PBS) and then inoculated into 15 mL conical tubes (BD Falcon, Franklin Lakes, N.J.) or tissue culture wells (Sarstedt, Inc., Newton, N.C.) containing DM.

Example 1

Trophozoites ($3.75 \times 10^5$ mL$^{-1}$) were washed in PBS (VWR, Radnor, Pa.) and inoculated into 10 mL of fresh DM. At time 0, each of the following treatment groups was added to culture tubes: Group 1) control: 0.5 mL DM; Group 2) 0.5 mL pluronic lecithin organogel (PLO; Pluronic F127); Group 3) 75 mg ponazuril (PO) (0.5 mL); Group 4) 50 mg oxibendazole (OX) (0.5 mL); Group 5) 37.5 mg PO (0.25 mL)+0.25 mL PLO; and Group 6) 25 mg OX (0.25 mL)+0.25 mL PLO.

PLO (Pluronic F127 Letco Medical, Decatur, Ala.) was combined with OX (Anthelcide EQ® Zoetis, Florham Park, N.J.) or PO (Marquis® Merial, Duluth, Ga.) paste formulations by shear force, syringe-to-syringe-blending using two luer-lock syringes and a rapid fill connector (Baxter, Inglewood, Calif.). Each treatment was applied to conical culture tubes in 5 replicates. Following growth at 37° C., samples were taken every 2 hours for a total of 12 hours, and the tubes were vortexed prior to removal of a 20 µL sample. From these samples, the surviving organisms were counted utilizing disposable Neubauer hemocytometers (C-Chip® NanoEnTek Inc., Pleasanton, Calif.). At 12 hours post-treatment, each formulation was recultured in fresh DM without antiprotozoal compound and evaluated microscopically daily for the presence of *T. foetus* organisms in culture. These assays were performed in order to evaluate if the effects exerted by the antiprotozoal compounds could be reversed.

The inhibitory effects of PO and OX significantly inhibited parasite growth at concentrations of 75 mg mL$^{-1}$ and 50 mg mL$^{-1}$, respectively. Both PO alone and OX alone demonstrated a 98% reduction in motile organisms after 2 hours of culture. However, following re-culture at 12 hours and examination at 24 hours, reestablishment of motile organisms was observed.

A significant decrease in the number of trichomonads was also noted with PLO combined with OX and with PLO combined with PO, and their respective cultures were found to be negative for motile trophozoites at 24 hours post treatment. However, motile organisms were once again present at 48 hours with restoration of culture to original growth (see FIG. 1).

Example 2

Trophozoites ($9.5 \times 10^5$ mL$^{-1}$) were cultured as described above and added to tissue culture wells with 3 mL of DM. At time 0, each of the following treatment groups were added to tissue culture wells: Group 1) control 4 mL DM; Group 2) 4 mL PLO; Group 3) 150 mg oxfendazole (OXF)+1 mL PLO; and Group 4) 450 mg PO (3 mL)+1 mL PLO.

The OXF (U.S. Pharmacopeial Convention Rockville, Md.) stock solution was made in EtOH (Humco Texarkana, Tex.) and mixed with Velvachol ("VC"; Valeant North America LLC, Bridgewater, N.J.) and thereafter was stored at 150 mg mL$^{-1}$. PLO was combined with OXF stock solution or PO by shear force by syringe-to-syringe mixing. Each treatment was applied to tissue culture wells in duplicate. Following growth at 37° C. on a rocker plate (Hoefer Inc., Holliston, Mass.), samples were collected every 4 hours for a total of 24 hours. A 20 µL sample was removed from each well, and the surviving organisms were counted utilizing disposable Neubauer hemocytometers.

At 8 hours post-treatment, each formulation was removed from the tissue culture well and centrifuged at 4000 g for 10 minutes. The supernatant was removed and the pellet was re-suspended in either PBS+Compound or DM+Compound and re-incubated at 37° C. Assays were microscopically examined every 4 hours for a total of 24 hours for the presence of *T. foetus* organisms in culture by counting organisms as described in Example 1.

The concentration of benzimidazole was increased with the use of OXF solution at 150 mg mL$^{-1}$. Oxfendazole combined with PLO had substantial inhibitory effects on trichomonad growth, inducing the pseudocyst or endoflagellar state with no motile trichomonads in the culture following an incubation period of 4 hours. The pseudocyst state was maintained for 24 hours and reversibility of the organism was not demonstrated (see Table 1).

DMSO (VedCo, Saint Joseph, Mo.). The combinations of PLO (Pluronic F127 Letco Medical, Decatur, Ala.), VC (Valeant North America LLC, Bridgewater, N.J.), EtOH (Humco Texarkana, Tex.), and OXF stock solution were mixed as described above.

Each treatment was applied to tissue culture wells in duplicate. Following culture as described in Example 2, samples were collected every 8 hours for a total of 24 hours

TABLE 1

OXF solution when combined with PLO and added to culture induced pseudocyst formation 4 hours following inoculation. Cultures remained negative for motile trophozoites for 24 hours with no reversibility noted.

|  | 4 hours post-incubation | 8 hours post-incubation | 12 hours post-incubation | 16 hours post-incubation | 21 hours post-incubation | 24 hours post-incubation |
|---|---|---|---|---|---|---|
| Control | 947,500 | 952,500 | 938,500 | 945,000 | 927,500 | 928,000 |
| PO + PLO | no visibility | — | — | — | — | — |
| PLO | no visibility | — | — | — | — | — |
| OXF + PLO | pseudocysts | pseudocysts | pseudocysts | pseudocysts | pseudocysts | pseudocysts |

Example 3

Trophozoites (5×10$^4$ mL$^{-1}$) were cultured as described above and added to all tissue culture wells along with 3 mL of DM for a total volume of 4 mL of DM with 50,000 organisms per well. At time 0, each of the following treatment groups were added to tissue culture wells as follows: Group 1) positive control 4 mL DM; Group 2) negative control 4 mL 70% ethanol (EtOH); Group 3) 150 mg oxfendazole solution (OXF) (1 mL)+2 mL Velvachol (VC)+1 mL PLO; Group 4) 150 mg OXF (1 mL)+3 mL VC; Group 5) 150 mg OXF (1 mL) +3 mL EtOH; Group 6) 150 mg OXF (1 mL)+2 mL EtOH+1 mL PLO; Group 7) 1 mL EtOH +2 mL VC+1 mL PLO; Group 8) 1 mL EtOH+3 mL VC; Group 9) 3 mL EtOH+1 mL PLO; Group 10) 4 mL EtOH; Group 11) 4 mL VC; Group 12) 150 mg oxfendazole dissolved in 4 mL 99% DMSO; and Group 13) 4 mL 99% DMSO.

The OXF (U.S. Pharmacopeial Convention Rockville, Md.) stock solution was made in EtOH (Humco Texarkana, Tex.) and stored at 150 mg mL$^{-1}$, with the exception of Formulation 13 which included OXF dissolved in 99% and counted as previously described. At 24 hours post-treatment and following counting of organisms, each formulation was removed from the tissue culture well and centrifuged at 4000 g for 10 minutes. The supernatant was removed and placed in a labeled vial for evaluation of drug concentration at a later time. The pellet was re-suspended in 4 mL of DM and placed once again in a tissue culture well before being re-incubated at 37° C. This process was repeated every 24 hours for 5 passages (120 hours) to allow for re-emergence of any organisms. Assays were continued to be microscopically examined during this period for the presence of T. foetus organisms in culture by counting of live organisms.

Again, OXF solution when combined with PLO rapidly induced the pseudocyst stage and complete kill of organisms following continued culture of 5 days. Additionally, EtOH and 99% DMSO were also capable of inducing death of trophozoites with subsequent negative cultures over a 5 day period (see Table 2).

TABLE 2

The formation of pseudocysts was once again rapidly induced by the addition of OXF solution combined with PLO. In addition, each component of the OXF solution + PLO formulation was tested in all possible combinations to determine ability to induce pseudocyst formation. Ethanol 70% and DMSO 99% both rapidly induced death of trophozoites. All cultures were negative for reversibility of organisms following 5 days (120 hours) of culture.

|  | 8 hours post-incubation | 16 hours post-incubation | 24 hours post-incubation | 48 hours post-incubation | 72 hours post-incubation | 96 hours post-incubation | 120 hours post-incubation |
|---|---|---|---|---|---|---|---|
| Control + DM | 51,500 | 49,500 | 52,000 | 57,500 | 55,500 | 32,000 | 12,500 |
| Control + EtOH | dead trophs | dead trophs | dead trophs | dead trophs | dead trophs | no cells | no cells |
| OXF + EtOH + VC + PLO | pseudocysts | pseudocysts | pseudocysts | pseudocysts | pseudocysts | no cells | no cells |
| OXF + EtOH + VC | pseudocysts | pseudocysts | pseudocysts | pseudocysts | pseudocysts | no cells | no cells |
| OXF + EtOH | pseudocysts | pseudocysts | pseudocysts | pseudocysts | pseudocysts | no cells | no cells |
| OXF + EtOH + PLO | pseudocysts | pseudocysts | pseudocysts | pseudocysts | pseudocysts | no cells | no cells |
| EtOH + VC + PLO | pseudocysts | pseudocysts | pseudocysts | pseudocysts | pseudocysts | no cells | no cells |
| EtOH + VC | pseudocysts | pseudocysts | pseudocysts | pseudocysts | pseudocysts | no cells | no cells |
| EtOH + PLO | pseudocysts | pseudocysts | pseudocysts | pseudocysts | pseudocysts | no cells | no cells |
| EtOH | dead trophs | dead trophs | dead trophs | dead trophs | dead trophs | no cells | no cells |
| VC | pseudocysts | pseudocysts | pseudocysts | pseudocysts | pseudocysts | no cells | no cells |
| OXF + DMSO | no visibility | no visibility | no visibility | pseudocysts | pseudocysts | no cells | no cells |
| DMSO | dead trophs | dead trophs | dead trophs | dead trophs | dead trophs | no cells | no cells |

Example 4

Objective 1:

The first objective can be designed to evaluate the efficacy of veterinary formulations on *T. foetus* organisms in in vitro cultures, wherein the veterinary formulations may or may not contain a a polymer enhancer (PPE). For example, a PPE may be an emollient. The PPE can be evaluated to increase permeability of the stratum corneum to antiprotozoal compounds and also to allow for sustained release of the antiprotozoal compounds. The instant example can utilize five replications of each treatment to investigate variations in efficacy and to evaluate the survivability of pseudocysts (an alternate, viable, non-motile stage of the *T. foetus* life cycle).

The *T. foetus* isolate of bovine origin (11457) can be maintained at −80° C. and cultured in Diamond's Media (DM) at 37° C. Following culturing, $1 \times 10^5$ of *T. foetus* organisms can be washed and resuspended in 1 mL of sterile phosphate buffered saline (PBS), and then inoculated into tubes containing 10 mL of DM. At time 0, one of the following treatment groups can be added to individual culture tubes as follows: 1) 0.5 mL DM (control); 2) 0.5 mL PPE; 3) 75 mg PO (0.5 mL); 4) 50 mg OX (0.5 mL); 5) 37.5 mg PO (0.25 mL)+0.25 mL PPE; or 6) 25 mg OX (0.25 mL)+0.25 mL PPE. Each treatment group can be applied to individual culture tubes in 5 replicates. The tubes can be vortexed and a 20 µL sample can be removed every 2 hours for a total of 12 hours.

From each sample, the surviving organisms can be counted utilizing disposable Neubauer hemocytometers (JK). At 12 hours post-treatment, each formulation can be recultured in fresh DM and can be evaluated microscopically daily for 7 days for the presence of *T. foetus* organisms in culture. This will ensure that the organism does not survive treatment in the pseudocyst stage, thus creating a false negative result. Based on the results from objective 1, one or more formulations (e.g., formulations with the fastest and highest percentage kill of *T. foetus* organisms) can be chosen for use in objective 2.

Objective 2:

The second objective can be to determine the safety of the most efficacious formulation identified in objective 1 by applying it to the prepuce of *T. foetus* negative bulls. Six *T. foetus* negative yearling bulls can be utilized to conduct a safety study under the Center for Veterinary Medicine (CVM), Food and Drug Administration (FDA), Guidance for Industry (GFI) #38 for Effectiveness Evaluations of Topical Animal Drugs under skin/wound antibiotic/antifungal category.

Removal of contaminating organisms can be performed by thoroughly washing the prepuce and penis of the bull with soapy water to facilitate removal and breakdown of smegma and any associated biofilms. This can allow for adequate contact of the formulation on the penis and prepuce and fulfill appropriate testing guidelines of the new animal drug against the primary pathogen in question. Each of the six bulls can then have 100 mL of the selected veterinary formulation(s), as defined in objective 1, applied topically to the penis and prepuce as a single application. One bull can serve as a negative control and will have 100 mL of sterile 0.9% $NaCL_2$ applied to the penis and prepuce.

Each of the six bulls can be examined on day 0, initial day of application of the formulation, daily for the first week, and then weekly for a total of 4 weeks for any signs of inflammation, irritation or tissue damage. A clinical scoring system can be utilized to facilitate an objective evaluation of the penis and prepuce. The scoring system can use a scale of 1 to 4:1=no redness or edema, 2=slight redness and slight edema, 3=moderate redness and moderate edema, 4=severe redness, severe edema, and ulcerations.

Example 5

A total of ten beef bulls positive for *T. foetus* and culture negative for *Campylobacter fetus* and *Histophilus somni* can be utilized in this study. Bulls can be tested for *T. foetus* via preputial scraping for smegma and PCR two weeks prior to arrival and again upon arrival at the study site. Only bulls tested positive for *T. foetus* via PCR can be included in study.

Bulls can be fed Coastal Bermuda grass hay free choice, soy hull and corn gluten pellets with ad libitum access to clean water. On day 0, cultures of the penis and prepuce can be collected via sterile mare uterine culture swabs. All cultures can be cultured for aerobic and anaerobic bacteria and sensitivity. The prepuce and penis of the bull can be thoroughly washed with liquid detergent and water to facilitate removal and breakdown of smegma and any associated biofilms. This can allow for adequate contact of the therapeutic formulation on the penis and prepuce and fulfill appropriate testing guidelines of the new animal drug against the primary pathogen in question.

Following washing of the penis and prepuce, a culture swab of the penis and prepuce and preputial scraping can be collected. Following washing and testing, the dorsal nerve of the penis can be blocked by administration of 2 mL subcutaneously of 2% lidocaine. A penrose drain can be placed around the distal portion of the penis and sutured with simple interrupted sutures using 2-0 PDS suture. Placement of the penrose drain can facilitate removal of urine from the prepuce in order to prevent urine from removing the treatments from the penis and prepuce. The PLO gel can then be topically applied to the penis and the prepuce to control for the PLO gel's effect on the *T. foetus*. The PLO gel is a vehicle which has been approved for topical use. One hundred mLs of the gel can be manually applied to the extended penis and prepuce in a manner that can ensure complete coverage of the penile and preputial epithelium. Cultures and preputial smegma can again be collected on day 7 and then weekly until day 30 of the study.

The penrose drain and sutures holding it in place can be removed on day 7. The penrose drain can be placed into sterile red top tube and submitted for culture and biofilm formation. All preputial smegma samples can undergo PCR. If all PCRs are negative for *T. foetus* following application of the PLO gel then the bulls can be considered cured and the study can end. However, if any of the PCRs are positive following PLO gel treatment then the bulls can undergo a week of rest and be moved to phase II of the study.

On Day 0 of phase II of the study, the penis and prepuce can again be washed with liquid detergent and water and cultures and preputial smegma can again be collected and submitted. A penrose drain can again be placed as previously described to prevent urine from removing the Oxibendazole/PLO paste from the penis and prepuce. A paste made of 60 g of Oxibendazole powder mixed with buffered velvachol and mixed 1:1 with PLO gel can be topically massaged on the penis and the prepuce. Following treatment, each bull can be returned to their stall. Each bull can be closely observed following treatment for any signs of discomfort or altered behavior.

If any signs of irritation or inflammation on the penis and prepuce, the penis and prepuce can be immediately washed with liquid detergent and water to remove the gel and the study can be ended. If no irritation, cultures and preputial smegma can be collected from each bull 7 days following the administration of the Oxibendazole/PLO paste and then weekly until day 30. If any of the samples collected following the administration of the Oxibendazole/PLO paste are positive for *T. foetus*, the bull can undergo a resting period of one week. The bull can then be moved to phase III of the study.

Phase III can repeat all steps in phase II of the study but penile and preputial treatment with an increase amount of drug (120 grams of Oxibendazole/PLO combination) can be utilized. If the bull is positive any time following treatment with 120 grams of Oxibendazole/PLO combination then the bull can receive no further treatment and the study can end.

Preputial Scraping.

A preputial scraping involves utilizing a sterile mare infusion pipette attached to a 10 cc syringe. The mare infusion pipette can be placed in the preputial orifice and directed to the fornix of the prepuce by manual palpation. The prepuce can be massaged against the pipette while at the same time aspirating by pulling back on the plunger of the 10 mL syringe. After removing the pipette from the sheath, the sample can be immediately placed into 2 mL of modified Diamond's medium. The media can be pipetted up and down along the length of the pipette to remove any smegma in the pipette. All samples can be submitted PCR to test for presence of *T. foetus*.

Assessment of Bacteria and Biofilm.

A sterile culture swab covered by a protective outer sheath can be placed into the preputial cavity of the bull. Once inside the preputial cavity, the swab can be advanced beyond the protective outer sheath until it contacts the penis and the prepuce and can be gently rotated, collecting a sample of fluid and cells from the penis and the prepuce. The inner swab can then be withdrawn into the protective outer sheath, and the entire culture instrument can be withdrawn. Once outside the bull, the swab tip can be placed into a sterile culture tube. Additionally, following the removal of the penrose drain, the drain can be placed in a sterile red top tube and submitted for culture and biofilm formation. All cultures can undergo aerobic and anaerobic culture. Following culture of the penrose drains, the drains can undergo examination by electron microscopy for biofilm presence.

What is claimed is:

1. A veterinary formulation comprising i) a therapeutically effective amount of an antiprotozoal compound ii) a polymer lecithin organogel, and iii) an emollient, wherein the veterinary formulation is a gel or a paste.

2. The veterinary formulation of claim 1, wherein the antiprotozoal compound is oxfendazole.

3. The veterinary formulation of claim 1, wherein the antiprotozoal compound is oxibendazole.

4. The veterinary formulation of claim 1, wherein the antiprotozoal compound is albendazole.

5. The veterinary formulation of claim 1, wherein the antiprotozoal compound is ponazuril.

6. The veterinary formulation of claim 1, wherein the veterinary formulation comprises one or more second therapeutic agents.

7. The veterinary formulation of claim 1, wherein the veterinary formulation is a paste.

8. The veterinary formulation of claim 1, wherein the veterinary formulation is a gel.

9. A method of treating trichomoniasis in a bovine, said method comprising the step of administering the veterinary formulation of claim 1 to the bovine.

10. The method of claim 9, wherein the trichomoniasis is caused by *Tritrichomonas foetus*.

11. The method of claim 9, wherein the antiprotozoal compound is oxfendazole.

12. The method of claim 9, wherein the antiprotozoal compound is oxibendazole.

13. The method of claim 9, wherein the antiprotozoal compound is albendazole.

14. The method of claim 9, wherein the antiprotozoal compound is ponazuril.

15. The method of claim 9, wherein the administration is applied to a location on the prepuce of the bovine.

16. The method of claim 9, wherein the administration is applied to a location on the penis of the bovine.

17. The method of claim 9, wherein the method further comprises administration of one or more second therapeutic agents.

18. The method of claim 10, wherein the method of treating is performed until the *Tritrichomonas foetus* is no longer viable in the bovine.

19. The method of claim 9, wherein the veterinary formulation is a paste.

20. The method of claim 9, wherein the veterinary formulation is a gel.

* * * * *